United States Patent [19]

Thominet et al.

[11] Patent Number: 4,499,019

[45] Date of Patent: Feb. 12, 1985

[54] N-(1-ALLYL-2-PYRROLIDYLMETHYL)-2,3-DIMETHOXY-5-SULFAMOYLBENZAMIDE AND DERIVATIVES THEREOF AND METHOD FOR TREATING HOT FLUSHES ASSOCIATED WITH NATURAL OR SURGICAL MENOPAUSE

[75] Inventors: Michel L. Thominet; Jacques J. Perrot, both of Paris, France

[73] Assignee: Societe D'Etudes Scientifiques et Industrielles de l'Ile de France, Paris, France

[21] Appl. No.: 540,918

[22] Filed: Oct. 13, 1983

Related U.S. Application Data

[63] Continuation of Ser. No. 265,017, May 19, 1981, abandoned, which is a continuation of Ser. No. 82,510, Oct. 9, 1979, abandoned, which is a continuation of Ser. No. 928,028, Jul. 25, 1978, abandoned, which is a continuation of Ser. No. 815,756, Jul. 14, 1977, abandoned.

[30] Foreign Application Priority Data

Jul. 19, 1976 [FR] France ............................... 76 22180

[51] Int. Cl.³ .............................................. A61K 31/40
[52] U.S. Cl. ..................................... 514/428; 548/567
[58] Field of Search ...................... 424/274; 260/326.4

Primary Examiner—Stanley J. Friedman
Attorney, Agent, or Firm—Fitzpatrick, Cella, Harper & Scinto

[57] ABSTRACT

N-(1'-allyl-2'-pyrrolidylmethyl)-2,3-dimethoxy-5-sulfamoylbenzamide and derivatives thereof and method for treating the psycho neuro-vegetative syndrome of the natural or surgical menopause by administering an effective amount of said compound to a patient.

12 Claims, No Drawings

N-(1-ALLYL-2-PYRROLIDYLMETHYL)-2,3-DIMETHOXY-5-SULFAMOYLBENZAMIDE AND DERIVATIVES THEREOF AND METHOD FOR TREATING HOT FLUSHES ASSOCIATED WITH NATURAL OR SURGICAL MENOPAUSE

This application is a continuation of application Ser. No. 265,017 filed May 19, 1981, now abandoned, which is a continuation of Ser. No. 082,510 filed Oct. 9, 1979, now abandoned, which is a continuation of Ser. No. 928,028 filed July 25, 1978, now abandoned, which is a continuation of parent application Ser. No. 815,756 filed July 14, 1977 now abandoned.

This invention relates to a new compound N-(1'-allyl-2'-pyrrolidylmethyl)-2,3-dimethoxy-5-sulfamoylbenzamide and a method for treating the psycho neuro-vegetative syndrome of the natural or surgical menopause by administering to a patient suffering from the psycho neuro-vegetative syndrome a therapeutically effective amount of said compound sufficient to relieve the symptoms of the syndrome including hot flashes, vulvar irritation, headaches, anxiety, irritability, etc.

In the past the symptoms of the psycho neuro-vegetative syndrome caused by the natural or surgical menopause have normally been treated by administering to a patient hormonal compounds such as estrogen steroids and synthesized estrogens. Estrogens and other compounds having estrogenic action, however, have recently been suspected of causing cancer in patients resulting in considerable concern with respect to the use of these compounds.

Applicants have found that patients suffering from the psycho neuro-vegetative syndrome of the natural or surgical menopause may be successfully treated with N-(1'-allyl-2'-pyrrolidylmethyl)-2,3-dimethoxy-5-sulfamoylbenzamide to relieve the symptoms. The structure of the compound is fundamentally different from estrogen steroids or synthesized estrogens and consequently can be used without concern for side effects such as cancer. The pharmaceutical compound can be administered orally or subcutaneously. A marked decrease in the symptoms of the psycho neuro-vegetative syndrome of the natural or surgical menopause have been observed after treatment for only two days. The symptoms have been observed to disappear completely after treatment for as short a time as eight days.

The structural formula of N-(1'-allyl-2'-pyrrolidylmethyl)-2,3-dimethoxy-5-sulfamoylbenzamide according to the invention is as follows:

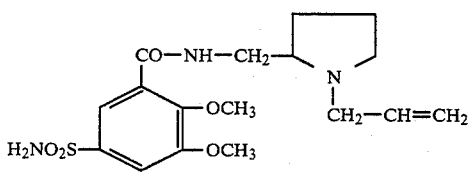

The compound may be prepared by reacting a compound of the following formula:

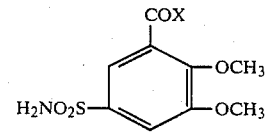

where X is hydroxyl, halogen or an organic residue, with 1-allyl-2-aminomethylpyrrolidine or a reactive derivative thereof.

In the initial compound, the organic residue contains groups capable of forming reactive acid derivatives including lower alkyl esters such as methyl, ethyl, propyl, butyl, isobutyl, pentyl and isopentyl esters; reactive acid esters such as methoxymethyl ester and cyanomethyl ester; substituted or unsubstituted aromatic or N-hydroxyimide esters; acid azides; acid hydrazides; symmetrical anhydrides; composite anhydrides, e.g. those formed from esters of carbonic acid and haloformic esters; azolides such as triazolides, tetrazolides and particularly imidazolides; substituted ω-trihaloacetophenones; substituted α-oxobenzeneacetonitriles; benzamides substituted on the nucleus, and other equivalent substances, and the compound of the formula:

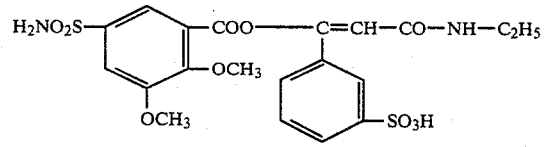

This compound is formed from 2,3-dimethoxy-5-sulphamoylbenzoic acid and an isoxazolium salt.

In the process for producing N-(1'-allyl-2'-pyrrolidylmethyl)-2,3-dimethoxy-5-sulfamoylbenzamide the reactive amine may be in the form of one of its reactive derivatives. Some examples are the reaction products of the amine with phosphorus chlorides; phosphorus oxychloride; dialkyl, diaryl, and orthophenylene chlorophosphites; alkyl or aryl dichlorophosphites; 1-allyl-2-aminomethylpyrrolidine isothiocyanate; symmetric or non-symmetric N-(1-allyl-2-pyrrolidylmethyl)-suphamides; N,N'bis-(1-allyl-2-pyrrolidylmethyl)urea; N-(1-allyl-2-pyrrolidylmethyl)enamine, and any other equivalent compound. The reactive derivatives described above can be reacted with the acid in situ or following preliminary isolation. The invention, however, is not restricted to the reactive derivatives described above.

It is alternatively possible to carry out the reaction between the free acid and the free amine in the presence of a condensing agent, e.g. silicon tetrachloride, phosphoric anhydride, a carbodiimide such as dicyclohexyl carbodiimide, or an alkoxyacetylene such as methoxyacetylene or ethoxyacetylene.

The amidifying reaction may be carried with or without a solvent. Some examples of suitable solvents which are inert vis-a-vis the amidifying reaction, include alcohols, polyols, benzene, toluene, dioxane, chloroform and diethyleneglycol dimethyl ether. An excess of the amine reactant may also be used as the solvent. Also, the reaction mixture may be heated during amidification, e.g. to the boiling point of the solvent.

The N-(1'-allyl-2'-pyrrolidylmethyl)-2,3-dimethoxy-5-sulfamoylbenzamide obtained by the above described method may optionally be reacted with pharmaceutically acceptable inorganic or organic acids such as hydrochloric, hydrobromic, sulphuric, phosphoric, oxalic, acetic, tartaric, citric and methanesulphonic acids to give acid-addition salts. Also the N-(1'-allyl-2'-pyrrolidylmethyl)-2,3-dimethoxy-5-sulfamoylbenzamide may be reacted with alkyl halides or sulphates to give quaternary ammonium salts.

The method of producing N-(1'-allyl-2'-pyrrolidylmethyl)-2,3-dimethoxy-5-sulfamoylbenzamide is more specifically illustrated by the following examples which are not to be considered restrictive with respect to either the method of preparation or possible applications:

EXAMPLE 1

N-(1'-allyl-2'-pyrrolidylmethyl)-2,3-dimethoxy-5-sulfamoylbenzamide 7.8 g (0.03 mole) of 2,3-dimethoxy-5-sulphamoylbenzoic acid, 200 ml of tetrahydrofuran and 7.3 g (0.045 mole) of carbonyl-diimidazole were placed in a 500-ml flask fitted with an agitator, a thermometer and a condenser. The mixture was agitated for 30 minutes at normal temperature after which 6.7 g (0.048 mole) of 1-allyl-2-aminomethylpyrrolidine was added. The mixture was left under agitation for 5 hours at 20° C. and then the solvent was evaporated under vacuum and the residue treated with 150 ml of water. The crystals were washed and dried. 6.9 g of N-(1'-allyl-2'-pyrrolidylmethyl)-2,3-dimethoxy-5-sulfamoylbenzamide was obtained. (Yield: 60%; melting point: 113°–114° C.)

EXAMPLE 2

N-(1'-allyl-2'-pyrrolidylmethyl)-2,3-dimethoxy-5-sulfamoylbenzamide

A 250-ml flask was used, fitted with an agitator, a thermometer and a bromine funnel. In this flask were placed 10.15 g (0.04 mole) of N-ethyl-5-phenyl-isoxazolium-3'-sulphonate, 100 ml of acetonitrile and, in small quantities at 0° C., a mixture of 10.4 g (0.04 mole) of 2,3-dimethoxy-5-sulphamoylbenzoic acid, 4.1 g (0.04 mole) of triethylamine and 80 ml of acetonitrile. The mixture was left for one hour at 0° C. and then for two hours at ambient temperature. 11.2 g (0.08 mole) of 1-allyl-2-amino-methylpyrrolidine was added drop by drop at 20° C. and the mixture was kept under agitation at ambient temperature for three hours. The crystals formed were filtered, washed with water and dried in an oven at 50° C. After crystallation in ethyl acetate 9.3 g of N-(1'-allyl-2'-pyrrolidylmethyl)-2,3-dimethoxy-5-sulfamoylbenzamide was obtained. (Yield: 61%; melting point: 117°–118° C.).

EXAMPLE 3

N-(1'-allyl-2'-pyrrolidylmethyl)-2,3-dimethoxy-5-sulfamoylbenzamide 55 g (0.2 mole) of methyl 2,3-dimethoxy-5-sulphamoylbenzoate and 275 ml of glycol were poured into a 500 ml flask fitted with an agitator and a thermometer. Dissolution was obtained at about 85° C. after which the mixture was cooled to 50° C. 35 g of 1-allyl-2-aminomethylpyrrolidine was added and the reaction mixture was heated to 50° C. until a test sample was totally soluble in dilute hydrochloric acid. When the reaction was complete 1 liter of water was added and the mixture was extracted with methylene chloride. When the solvent had evaporated the solid obtained was drained, washed with water and re-crystallized in 50% alcohol. 50.5 g of N-(1'-allyl-2'-pyrrolidylmethyl)-2,3-dimethoxy-5-sulfamoylbenzamide was obtained. (Yield: 66%; melting point: 108°–110° C.).

EXAMPLE 4

N-oxide of N-(1'-allyl-2'-pyrrolidylmethyl)-2,3-dimethoxy-5-sulfamoylbenzamide 200 ml of acetone and 28 g of 1-allyl-2-aminomethylpyrrolidine were placed in a 500-ml flask fitted with a thermometer and an agitator. 50 g of 2,3-dimethoxy-5-sulphamoylbenzoyl chloride was stirred into the flask while the temperature was kept between 10° and 15° C. Agitation of the mixture was continued for one hour at +10° C. and then 10 ml of ethanolic hydrochloric acid (30g/100 ml) was added. When agitation had stopped the acetone was decanted and 100 ml of absolute ethanol added. After the mixture had been left to stand for one hour, the crystals obtained were filtered, washed with 20 ml of absolute ethanol and then dried at 50° C. 56.3 g of N-(1'-allyl-2'-pyrrolidylmethyl)-2,3-dimethoxy-5-sulfamoylbenzamide hydrochloride was obtained. (Yield: 75%).

The hydrochloride obtained was dissolved in 170 ml of water and the mixture was then heated to about 40° C. and 600 g of active carbon (Acticarbone 3S) was added. Agitation of the mixture was continued for 10 minutes and then, after filtering, 110 ml of ethanol was added. The solution was treated with 25 ml of ammonia of specific gravity 0.89. The solid formed by cooling to 10° C. was filtered, washed with water and dried in a stove at 50° C. After re-crystallization in absolute ethanol 45 g of N-(1'-allyl-2'-pyrrolidymethyl)-2,3-dimethoxy-5-sulfamoylbenzamide was obtained. (Yield: 65.6%; melting point: 112°–114.5° C.).

The benzamide obtained was stirred into 150 ml of absolute ethanol and then 25 ml of hydrogen peroxide of volume strength 110 was added. The mixture was heated to 30° C. for 20 hours and then 1 g of manganese dioxide was added in small quantities and the mixture simultaneously cooled. The mixture was kept under agitation for 30 minutes and was filtered following the addition of 4 g of active carbon (Acticarbone 3S). After the addition of 250 ml of acetone the compound crystallized out at ambient temperature. After recrystallization in water 27.5 g of the N-oxide of N-(1'-allyl-2'-pyrrolidylmethyl)-2,3-dimethoxy-5-sulfamoylbenzamide was obtained. (Yield: 59%; melting point: 170° C. with decomposition).

EXAMPLE 5

N-(1'-allyl-2'-pyrrolidylmethyl)-2,3-dimethoxy-5-sulfamoylbenzamide 7.2 g of succinimide-2,3-dimethoxy-5-sulphamoylbenzoate and 50 ml of dimethylformamide were placed in a 250-ml flask fitted with an agitator, a thermometer and a bromine funnel, and 3.7 g of 1-allyl-2-aminomethylpyrrolidine was dropped in. The temperature of the mixture increased and reached 36° C. by the time all the amine has been introduced. After one hour's reaction the solvent was evaporated under vacuum and the residue dissolved hot in 50 ml of normal hydrochloric acid. The solution was made alkaline with 12 ml of 33% soda lye. The crystals obtained by cooling were filtered, washed with water and dried in a stove at 50° C. After recrystallization from absolute ethanol 4.4 g of N-(1'-allyl-2'-pyrrolidylmethyl)-2,3-dimethoxy-5-sulfamoylbenzamide was obtained. (Yield: 57.4%; melting point: 128° C.).

EXAMPLE 6

N-(1'-allyl-2'-pyrrolidylmethyl)-2,3-dimethoxy-5-sulfamoylbenzamide 20.3 g of phthalimide-2,3-dimethoxy-5-sulfamoylbenzoate and 110 ml of dimethylformamide were placed in a 500-ml flask, fitted with an agitator, a thermometer and a bromine funnel, and 9.1 g of 1-allyl-2-aminomethylpyrrolidine was added drop by drop. After a reaction lasting one hour the solvent was evaporated under vacuum and the residue dissolved in 100 ml of normal hydrochloric acid at boiling temperature. The solution was filtered hot and the filtrate made alkaline with 23% ammonia (pH: 9–10). The crystals which appeared on cooling were filtered, washed in water and dried in a stove at 50° C. After recrystallization from absolute ethanol 13.3 g of N-(1'-allyl-2'-pyrrolidylmethyl)-2,3-dimethoxy-5-sulfamoylbenzamide was obtained. (Yield: 69.4%; melting point: 128° C.).

EXAMPLE 7

N-(1'-allyl-2'-pyrrolidylmethyl)-2,3-dimethoxy-5-sulfamoylbenzamide bromomethylate 30 g of the cyanomethyl ester of 2,3-dimethoxy-5-sulphamoyl benzoic acid, 140 ml of xylene and 28 g of 1-allyl-2-aminomethylpyrrolidine were placed in a 250ml flask fitted with an agitator, a thermometer and a condenser. The mixture was heated for 15 minutes to reflux temperature; after cooling to room temperature the organic phase was extracted three times with 100 ml of 20% hydrochloric acid. The product, precipitated by adding 23% ammonia to the aqueous phase, was filtered, washed with water and dried in an oven at 50° C. After recrystallization in ethyl acetate, 27.9 g of N-(1'-allyl-2'-pyrrolidylmethyl)-2,3-dimethoxy-5-sulfamoylbenzamide was obtained. (Yield: 72.8%; melting point: 117°–118° C.).

The benzamide was dissolved in 110 ml of acetone. After cooling to 15° C., a solution of 7.5 g of methyl bromide in 20 ml of acetone was added. The mixture was left to stand at room temperature and the crystals formed were drained, washed with acetone and dried at 50° C. and then re-dissolved hot in 20 ml of methanol, treated with carbon black and filtered. The crystals formed after the addition of acetone were drained, washed with acetone and dried in a stove at 50° C. 20 g of bromomethylate of N-(1'-allyl-2'-pyrrolidylmethyl)-2,3-dimethoxy-5-sulfamoylbenzamide was obtained. (Yield: 57.3%;melting point: 125° C.).

EXAMPLE 8

Dextrorotatory N-(1'-allyl-2'-pyrrolidylmethyl)-2,3-dimethoxy-5-sulfamoylbenzamide 135 g of methyl-2,3-dimethoxy-5-sulphamoylbenzoate and 670 ml of ethylene glycol were placed in a 2-liter flask. Dissolution was obtained at about 85° C. and then the mixture was cooled to about 55° C. 82.5 g of dextrorotary 1-allyl-2-aminomethylpyrrolidine was added and the reaction mixture heated to 50° C. until a test sample was totally soluble in dilute hydrochloric acid. When the reaction was complete 3.5 liters of water was added and the mixture extracted with methylene chloride. When the solvent had evaporated the solid formed was drained, washed with water, recrystallized from absolute alcohol and dried at 40° C. 128 g of dextrorotatory N-(1'-allyl-2'-pyrrolidylmethyl)-2,3-dimethoxy-5-sulfamoylbenzamide was obtained. (Yield: 68%; melting point: 144°–145° C.) $(\alpha)_D^{20} = +63°$ (solution at 5% in dimethyl-formamide).

EXAMPLE 9

Laevorotatory N-(1'-allyl-2'-pyrrolidylmethyl)-2,3-dimethoxy-5-sulfamoylbenzamide 135 g of methyl-2,3-dimethoxy-5-sulphamoylbenzoate and 675 ml of ethylene glycol were placed in a 2-liter flask. Dissolution was obtained at about 85° C. and then the mixture was cooled to about 55° C. 83 g of laevorotatory 1-allyl-2-aminomethylpyrrolidine was added, and the reaction mixture was heated to 50° C. until a test sample was totally soluble in dilute hydrochloric acid. When the reaction was completed 3.5 liters of water was added and the mixture was extracted with methylene chloride. When the solvent had evaporated the solid formed was drained, washed with water, recrystallized from absolute alcohol and dried at 40° C. 120 g of laevorotatory N-(1'-allyl-2'-pyrrolidylmethyl)-2,3-dimethoxy-5-sulfamoylbenzamide was obtained. (Yield: 54%; melting point: 144°–145° C.) $[\alpha]_D^{20} = -62°8$ (solution at 5% in dimethyl-formamide).

N-(1'-allyl-2'-pyrrolidylmethyl)-2,3-dimethoxy 5-sulfamoylbenzamide can be incorporated in capsules, tablets, sugar-coated pills, granules, injectable solutions, etc., the preparations of which are known. Additional substances that do not react with the compound may be included, such as lactose, magnesium stearate, starch, talc, celluloses, levilite, alkali metal lauryl sulphates, saccharose and the usual vehicles used in midicinal preparations.

N-(1'-allyl-2'-pyrrolidylmethyl)-2,3-dimethoxy-5-sulfamoylbenzamide may be administered to patients suffering from the psycho neuro-vegetative syndrome of the natural or surgical menopause in the daily dosage range of from about 50–600 mg. A more preferred range is about 50–300 mg per day, the most preferred daily dosage being about 100 mg per day.

The following examples are representative pharmaceutical preparations in the form of capsules, injectable solutions, tablets and granules containing N-(1'-allyl-2'-pyrrolidylmethyl)-2,3-dimethoxy-5-sulfamoylbenzamide. These pharmaceutical preparations are made in a conventional manner.

EXAMPLE 10

| Capsules | |
|---|---|
| N—(1'-allyl-2'-pyrrolidylmethyl)-2,3-dimethoxy-5-sulfamoylbenzamide | 100.00 mg |
| Lactose | 60.00 mg |
| Starch | 29.00 mg |
| Microcrystalline cellulose | 46.00 mg |
| Sodium laurylsulphate | 1.00 mg |
| Methylcellulose 1500 | 1.00 mg |
| Talc | 6.40 mg |
| Magnesium stearate for capsule | 6.60 mg |

EXAMPLE 11

| Injectable Solution | |
|---|---|
| N—(1'allyl-2'-pyrrolidylmethyl)-2,3-dimethoxy-5-sulfamoylbenzamide | 100 mg |
| Isopropyl ether of propylene glycol | q.s. 2 ml |

EXAMPLE 12

| Injectable Solution | |
|---|---|
| N—(1'-allyl-2'-pyrrolidylmethyl)-2,3-dimethoxy-5-sulfamoylbenzamide | 100 mg |
| Triethylene glycol q.s. | 2 ml |

EXAMPLE 13

| Injectable Solution | |
|---|---|
| N—(1'-allyl-2'-pyrrolidylmethyl)-2,3-dimethoxy-5-sulfamoylbenzamide | 100 mg |
| Propylene glycol q.s. | 2 ml |

In the preparation of injectable solutions, it is also possible to dissolve N-(1'-allyl-2'-pyrrolidylmethyl) 2,3-dimethoxy-5-sulfamoylbenzamide in hydrochloric, levulinic, gluconic and glucoheptonic acids. The sterily prepared solution is made isotonic by an alkali metal chloride such as sodium chloride after which preservatives are added. Alternatively, the injectable solutions may be prepared without adding preservatives; the ampoule is filled under nitrogen and sterilized for one-half hour at 100° C.

EXAMPLE 14

| Capsules | |
|---|---|
| N—(1'-allyl-2'-pyrrolidylmethyl)-2,3-dimethoxy-5-sulfamoylbenzamide | 50.00 mg |
| Lactose | 30.00 mg |
| Starch | 14.50 mg |
| Microcrystalline cellulose | 23.00 mg |
| Sodium laurylsulphate | 0.50 mg |
| Methylcellulose 1500 cps | 0.50 mg |
| Talc | 3.20 mg |
| Magnesium stearate for capsule | 3.30 mg |

EXAMPLE 15

| Tablets | |
|---|---|
| N—(1'-allyl-2'-pyrrolidylmethyl)-2,3-dimethoxy-5-sulfamoylbenzamide | 100.00 mg |
| Dried starch | 26.68 mg |
| Lactose | 11.50 mg |
| Methylcellulose 1500 cps | 1.32 mg |
| Magnesium stearate | 2.00 mg |
| Talc | 1.00 mg |
| Silica | 7.50 mg |

In preparing tablets N-(1'-allyl-2'-pyrrolidylmethyl)-2,3-dimethoxy-5-sulfamoylbenzamide is mixed with dried starch and lactose by the successive dilution method. The mixture is granulated with methylcellulose after which levilite, magnesium stearate and talc are added to the granulated mixture before being compressed to form the tablets. Microcrystalline cellulose is used as a thickening agent though other known thickening agents may be used such as veegum.

EXAMPLE 16

| Tablets | |
|---|---|
| N—(1'-allyl-2'-pyrrolidylmethyl)-2,3-dimethoxy-5-sulfamoylbenzamide | 100.00 mg |
| Microcrystalline cellulose (dried Avicel PH 102) | 180.00 mg |
| 25% aqueous solution of dried PH 102 Avicel | 46.31 mg |
| Talc | 7.50 mg |
| Levilite | 17.50 mg |
| Magnesium stearate | 8.69 mg |

Methylcellulose is used as a granulating agent though other appropriate granulating agents may be used as for example ethylcellulose, polyvinylpyrrolidone, starch paste, gum arabic, etc. Starch is used as a disintegrating agent though alternative disintegrating agents include maize starch, carboxymethyl starch, alginate, microcrystalline cellulose, etc.

EXAMPLE 17

| Granules | |
|---|---|
| N—(1'-allyl-2'-pyrrolidylmethyl)-2,3-dimethoxy-5-sulfamoylbenzamide | 100.00 mg |
| Dried starch | 26.68 mg |
| Lactose | 11.50 mg |
| Methylcellulose 1500 cps | 1.32 mg |
| Magnesium stearate | 2.00 mg |
| Talc | 1.00 mg |
| Levilite | 7.50 mg |

N-(1'-allyl-2'-pyrrolidylmethyl)-2,3-dimethoxy-5-sulfamoylbenzamide exists in five allotropic forms which are characterized by their respective infrared spectrum and melting point as follows:

| Crystalline Form | Melting Point |
|---|---|
| $\alpha$ | 117–118° C. |
| $\beta$ | 102–114° C. |
| $\gamma$ | 128.5–129.5° C. |
| $\delta$ | 112.5–115° C. |
| $\epsilon$ | 96.5–99° C. |

(The melting points were measured on a BUCHI SMP-20 machine, the rise in temperature being at the rate of 1° C. per minute and the pre-heating temperature being at 100°–105° C.).

N-(1'-allyl-2'-pyrrolidylmethyl)-2,3-dimethoxy-5-sulfamoylbenzamide, which has remarkable pharmacological properties in the endocrine field, has been found to have very low toxicity which is entirely compatible with therapeutic use. The acute toxicity of the compound was studied in the Swiss mouse with both parenteral and oral administration and in the Wistar rat with oral administration. The results of the studies in the mouse are given in the following table:

| $LD_{50}$ BASE mg/kg | |
|---|---|
| Administered intravenously | 124–129 mg/kg |
| Administered intraperitoneally | 320 mg/kg |
| Administered subcutaneously | 465–518 mg/kg |
| Administered orally | 1,300 mg/kg |

In the rat the toxicity of the compound was so low that the LD$_{50}$ could not be determined; a dose of 4 g/kg, which is the maximum dosage that can be administered orally to animals, proved to be below the LD$_{100}$. However, the LD$_0$ is approximately 1.5 g/kg.

The semichronic toxicity of N-(1'-allyl-2'-pyrrolidylmethyl)-2,3-dimethoxy-5-sulfamoylbenzamide was studied in the Wistar rat and the Beagle dog with oral administration over a period of four weeks. In the rat the compound was administered in doses of 0.5, 1 and 2 g/kg per 24 hours. The compound was found to be relatively or completely non-toxic up to 1 g/kg per 24 hours. In the Beagle dog treatment with doses of 50 and 100 mg/kg per 24 hours was tolerated well. These results show that the toxicity of the compound is remarkably low.

N-(1'-allyl-2'-pyrrolidylmethyl)-2,3-dimethoxy-5-sulfamoylbenzamide has virtually no cataleptic action. The compound was administered subcutaneously to male rats. The criterion for the cataleptic state was the immobility of the animal for 30 seconds with its front limbs apart and arranged carefully on cubes of wood 4 centimeters high, thus placing the animal in an unaccustomed and uncomfortable position. The cataleptic action was measured with the effect of the administered compound at its maximum, i.e. 5-6 hours after the compound had been administered. It was found that a dose as high as 200 mg/kg administered subcutaneously made only 30% of the animals cataleptic after six hours. Thus, the compound may be used clinically with good tolerance vis-a-vis the extra-pyramidal system.

Tests carried out on several animal species have drawn attention to properties of N-(1'-allyl-2'-pyrrolidylmethyl)-2,3-dimethoxy-5-sulfamoylbenzamide useful in therapeutic applications in the endocrino-gential sphere. Experiments have been carried out on both the female rat and the female hamster. The changes produced by the compound at the level of the ovary and of vaginal cytology make it possible to predict a point of impact located at the level of the hypothalamo hypophyso-ovarian axis.

Administration of the compound by subcutaneous injections in doses of 3.5 and 10 mg/kg to the female rat and the female hamster caused the corpora lutea of the ovary to be maintained. The corpora lutea thus maintained secreted increased quantities of progesterone.

In the female rat the vaginal cycle was blocked in dioestrus although there was little change to the uterus. The vaginal epithelium was primsmatic, indicating the predominance of progesterone over estrogens.

In the rat and hamster development of the mammary glands was noted with signs of secretory activity at the highest doses. The rat appeared to be more susceptible than the hamster.

The results of the experiments carried out on laboratory animals justified tests with N-(1'-allyl-2'-pyrrolidylmethyl)-2,3-dimethoxy-5-sulfamoylbenzamide in human medicine. Nearly 300 observations have established the clinical tolerance and the primary clinical indications of the compound. In 286 patients clinical and biological tolerance was excellent. Side effects including mammary congestion, galactorrhea, drowsiness, etc., were found in less than 8% of the cases. Twenty extended treatments (100-200 mg/24 hours), over half of which lasted more than six months, confirm good long term tolerance. Eight patients received doses of 300-600 mg per day for seven to eight months and in no case did the side effects make it necessary to stop the therapy.

Tests have established that N-(1'-allyl-2'-pyrrolidylmethyl)-2,3-dimethoxy-5-sulfamoylbenzamide is extremely effective in the psycho neuro-vegetative syndrome of the menopause, particularly hot flashes, vulvar pruritus and the vaginal diseases which accompany this period of a woman's genital life (84% of the cases treated).

The action of the compound on the psycho neuro-vegetative symptoms of the menopause has been studied with double blinding against placebo. Forty observations were found sufficient to prove the superiority of the compound over the placebo in view of the very significant difference between them (the probability of that superiority being due to chance was from 1/100 to 1/1,000). The following examples demonstrate the effectiveness of the compound.

EXAMPLE 18

A patient 51 years old, suffering considerable neuro-vegetative symptoms in the natural menopause mainly with attacks of sweating and hot flushes (30-40 a day), was treated orally with N-(1'-allyl-2'-pyrrolidylmethyl)-2,3-dimethoxy-5-sulfamoylbenzamide at a dosage of 100 mg per day. In two days a very marked decrease in the flashes and sweating attacks was observed (8 per day). These symptoms disappeared after treatment for eight successive days. The following is a comparison of the patient's neuro-vegetative symptoms before treatment with treatment after eight days:

|  |  | Before Treatment | After Treatment |
|---|---|---|---|
| Hot Flushes: | Frequency | Severe | None |
|  | Intensity | Severe | None |
| Headaches |  | Medium | None |
| Anxiety |  | Slight | None |
| Irritability |  | Severe | Slight |

The patient was treated for twenty days yet no side effects were observed and tolerance was perfect.

EXAMPLE 19

A patient 53 years old had a menopausal neuro-vegetative syndrome with mainly hot flushes which set in following a hysterectomy for an enormous fibroid tumor with hemorrhaging and salpingo-oophoritis.

The patient was treated orally with N-(1'-allyl-2'-pyrrolidylmethyl)-2,3-dimethoxy-5-sulfamoylbenzamide at a dosage rate of 100 mg per day. The results obtained were excellent after eight successive days of treatment. Tolerance was perfect and no side effects were observed. The results are shown below:

|  |  | Before Treatment | After Treatment |
|---|---|---|---|
| Hot Flushes: | Frequency | Severe | None |
|  | Intensity | Severe | None |
| Headaches |  | Severe | Slight |
| Anxiety |  | Medium | Slight |
| Irritability |  | Severe | Slight |

EXAMPLE 20

A patient 45 years old had considerable neuro-vegetative symptoms in the natural menopause with mainly hot flushes and headaches.

The patient was treated orally with N-(1'-allyl-2'-pyrrolidylmethyl)-2,3-dimethoxy-5-sulfamoylbenzamide at a dosage rate of 100 mg per day for twenty days. The hot flushes were found to disappear completely following eight successive days of treatment. Tolerance was perfect and the results of the treatment were excellent. The results are shown below:

|  |  | Before Treatment | After Treatment |
| --- | --- | --- | --- |
| Hot Flushes: | Frequency | Severe | None |
|  | Intensity | Severe | None |
| Headaches |  | Medium | None |
| Irritability |  | Severe | Slight |

EXAMPLE 21

A patient 55 years old had a menopausal neuro-vegetative syndrome with mainly hot flushes which set in following an operation for menopausal menometrorrhagia.

The patient was treated orally with N-(1'-allyl-2'-pyrrolidylmethyl)-2,3-dimethoxy-5-sulfamoylbenzamide at a dosage rate of 100 mg per day for twenty days. The hot flushes were found to disappear after five successive days of treatment. Tolerance was perfect and no side effects were observed. The results are shown below:

|  |  | Before Treatment | Twenty Days After Treatment |
| --- | --- | --- | --- |
| Hot Flushes: | Frequency | Severe | None |
|  | Intensity | Severe | None |
| Anxiety |  | Yes | No |
| Abdominal Meteorism |  | Yes | No |

Hot flushes and sweating appeared again four days after treatment was ended. The symptoms were as unpleasant as those before the first treatment. The patient was treated again in the same manner as previously at a dosage rate of 100 mg per day for twenty days. The effectiveness of the compound was as good as with the first treatment. The clinical tolerance was the same. No side effects were observed and the results of the treatment were excellent.

EXAMPLE 22

A patient 39 years old suffered neuro-vegetative symptoms in the surgical menopause with mainly hot flushes which set in following a hysterectomy for a fibroid tumor.

The patient was treated orally with N-(1'-allyl-2'-pyrrolidylmethyl)-2,3-dimethoxy-5-sulfamoylbenzamide at a dosage rate of 100 mg per day for a period of twenty days, though the symptoms disappeared after the first three successive days. The tolerance was perfect, no side effects were observed, and the results were excellent as indicated below:

|  |  | Before Treatment | Twenty Days After Treatment |
| --- | --- | --- | --- |
| Hot Flushes | Frequency | Medium | None |
|  | Intensity | Medium | None |
| Anxiety |  | Yes | No |
| Irritability |  | Yes | No |

EXAMPLE 23

A patient 58 years old had a natural menopausal neuro-vegetative syndrome with mainly hot flushes, depression, and attacks of sweating.

The patient was treated orally with N-(1'-allyl-2'-pyrrolidylmethyl)-2,3-dimethoxy-5-sulfamoylbenzamide at a dosage rate of 100 mg per day for twenty days. The results are indicated below:

|  |  | Before Treatment | Twenty Days After Treatment |
| --- | --- | --- | --- |
| Hot Flushes: | Frequency | Severe | Slight |
|  | Intensity | Severe | Slight |
| Anxiety |  | Yes | No |
| Irritability |  | Yes | Yes |
| Depression |  | Yes | No |
| Libido Change |  | Yes | Yes |

Hot flushes and sweating reappeared three days after treatment was terminated. However, after the patient was again treated with the same compound at a dosage rate of 100 mg per day for twenty days it was found that the second treatment was as effective as the first treatment. Symptoms appeared again five days after termination of the second treatment. The patient was again treated at the same dosage rate for the same period of time and the effectiveness of the treatment was found to be excellent as before. The tolerance was perfect and no side effects were observed.

The following table compares the results obtained after treating 243 patients with N-(1'-allyl-2'-pyrrolidylmethyl)-2,3-dimethoxy-5-sulfamoylbenzamide:

| Symptom | No. of Cases | Results Very Good & Good | Average & Zero | Percentage Very Good & Good |
| --- | --- | --- | --- | --- |
| Hot Flushes | 211 | 156 | 55 | 73.9% |
| Vulvar Irritation | 32 | 27 | 5 | 84% |

The results presented above establish the effectiveness of N-(1'-allyl-2'-pyrrolidylmethyl)-2,3-dimethoxy-5-sulfamoylbenzamide in the treatment of the psycho neuro-vegetative syndrome of the natural or surgical menopause. Its effectiveness was excellent or good in 74% of the cases of hot flushes and vulvar irritation was eliminated in 84% of the cases. These results were accompanied by parallel improvement in the patient's mental state.

The perfect acceptability of the treatment facilitated by its oral administration and its excellent general tolerance adds to the success of the compound in treating the psycho neuro-vegetative syndrome of the natural or surgical menopause. In no case was the course of treatment interrupted prematurely because a patient developed an aversion to it or because troublesome side effects emerged.

What is claimed is:

1. A method for treating hot flushes associated with natural or surgical menopause comprising administering to a patient suffering from said hot flushes a therapeutically effective amount, sufficient to reduce or eliminate symptoms of said hot flushes of a compound selected from the group consisting of N-(1'-allyl-2'-pyrrolidylmethyl)-2,3-dimethoxy-5-sulfamoylbenzamide and derivatives of said N-(1'-allyl-2'-pyrrolidylmethyl)-2,3-dimethoxy-5-sulfamoyl-benzamide.

2. A method according to claim 1 wherein said compound is administered parenterally to said patient.

3. A method according to claim 1 wherein the dosage of said compound administered to said patient is between about 50 and 600 mg/day.

4. A method according to claim 1 wherein the dosage of said compound administered to said patient is between about 100–300 mg/day.

5. A method according to claim 1 wherein the dosage of said compound administered to said patient is about 100 mg/day.

6. A method according to claim 1 wherein a pharmaceutically acceptable salt of said N-(1'-allyl-2'-pyrrolidylmethyl)-2,3-dimethoxy-5-sulfamoylbenzamide is administered to said patient.

7. A method according to claim 1 wherein said compound is administered orally to said patient.

8. A method according to claim 1 wherein the dextrorotatory form of said N-(1'-allyl-2'-pyrrolidylmethyl)-2,3-dimethoxy-5-sulfamoylbenzamide is administered to said patient.

9. A method according to claim 1 wherein the laevorotatory form of said N-(1'-allyl-2'-pyrrolidylmethyl)-2,3-dimethoxy-5-sulfamoylbenzamide is administered to said patient.

10. A method according to claim 1 wherein the N-oxide of N-(1'-allyl-2'-pyrrolidylmethyl)-2,3-dimethoxy-5-sulfamoylbenzamide is administered to said patient.

11. A method according to claim 1 wherein N-(1'-allyl-2'-pyrrolidylmethyl)-2,3-dimethoxy-5-sulfamoylbenzamide bromoethylate is administered to said patient.

12. N-(1'-allyl-2'-pyrrolidylmethyl)-2,3-dimethoxy-5-sulfamoyl benzamide and pharmaceutically acceptable salts thereof.

* * * * *